United States Patent [19]

Faust et al.

[11] 4,032,324

[45] June 28, 1977

[54] SYNERGISTIC HERBICIDAL COMPOSITION FOR THE CONTROL OF WEEDS

[75] Inventors: Wilfried Faust, Cologne; Kurt Westphal, Wuppertal-Vohwinkel, both of Germany

[73] Assignee: Bayer Aktiengesellschaft, Leverkusen, Germany

[22] Filed: Apr. 3, 1975

[21] Appl. No.: 565,028

Related U.S. Application Data

[62] Division of Ser. No. 885,367, Dec. 15, 1969, Pat. No. 3,909,234.

[30] Foreign Application Priority Data

Dec. 17, 1968   Germany .......................... 1815145

[52] U.S. Cl. ..................................... 71/93; 71/92; 71/120
[51] Int. Cl.$^2$ .......................................... A01N 9/22
[58] Field of Search ................................ 71/93, 120

[56] References Cited

UNITED STATES PATENTS

| 3,022,150 | 2/1962 | Weed | 71/93 |
| 3,402,040 | 9/1968 | Fassig | 71/93 |
| 3,544,570 | 12/1970 | Timmler et al. | 71/93 |
| 3,671,523 | 6/1972 | Westphal et al. | 71/93 |
| 3,905,801 | 9/1975 | Fanzi | 71/93 |

*Primary Examiner*—Glennon H. Hollrah
*Attorney, Agent, or Firm*—Burgess, Dinklage & Sprung

[57] ABSTRACT

Herbicidal compositions in the form of synergistic combinations of either 3-methylmercapto-4-amino-6-isopropyl-1,2,4-triazin-5-one or 3-methylmercapto-4-amino-6-tert.-butyl-1,2,4-triazin-5-one with either or both of N'-(3,4-dichlorophenyl)-N,N-dimethyl-urea and 3-amino-1,2,4-triazole, which are individually known compounds, which combinations possess synergistic herbicidal properties especially for the control of weeds.

7 Claims, No Drawings

SYNERGISTIC HERBICIDAL COMPOSITION FOR THE CONTROL OF WEEDS

The present invention relates to and has for its objects the provision for particular new herbicidal compositions in the form of synergistic combinations of either 3-methyl mercapto-4-amino-6-isopropyl-1,2,4-triazin-5- one or 3-methyl mercapto-4-amino-6-tert.-butyl-1,2,4-triazin-5-one with either or both of N'-(3,4-dichloro-phenyl)-N,N-dimethyl-urea and 3-amino-1,2,4-triazole, which are individually known compounds, which combinations possess outstanding synergistic herbicidal properties especially for the control of weeds, optionally in the form of carrier composition mixtures of such synergistic combinations with solid and/or liquid dispersible carrier vehicles, and methods for using such synergistic combinations in a new way especially for combating weeds, with other and further objects becombing apparent from a study of the within specification and accompanying examples.

It is known that triazinones such as 3-methyl mercapto-4-amino-6-isopropyl-1,2,4-triazin-5-one (1a) and 3-methylmercapto-4-amino-6-tert.-butyl-1,2,4-triazin-5one (1b) can be used as herbicides [compare Belgian Pat. No. 697,083].

It is also known that N'-(3,4-dichloro-phenyl)-N,N-dimethyl-urea (2a) [compare U.S. Pat. Nos. 2,655,445; 3,134,665; and 3,152,880; as well as German Pat. No. 970,425] and 3-amino-1,2,4-triazole (3a) [compare U.S. Pat. No. 2,670,282] are suitable alone or together for combating weeds.

All these active compounds, however, are selective herbicides and thus have the disadvantage that, when used as selective herbicides, they do not adequately destroy or control all of the wide variety of weeds which occur on uncropped land. Understandably, those weeds which are not controlled then spread unusually rapidly, since they grow without further rivalry from the other weeds which are controlled or destroyed by the given herbicide, and thus tend to negate the initial advantage of a given herbicidal treatment.

It has been found, in accordance with the present invention, that the particular new herbicidal compositions which comprise synergistic combinations of the active compounds
 i. 3-methylmercapto-4-amino-6-isopropyl-1,2,4-triazin-5-one or 3-methylmercapto-4amino-6-tert.-butyl-1,2,4-triazin-5-one of the formula

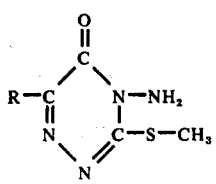

wherein R represents i-$C_3H_7$ (1a) or t-$C_4H_9$ (1b), with either or both of
 ii. N'-(3,4-dichloro-phenyl)-N,N-dimethyl-urea of the formula

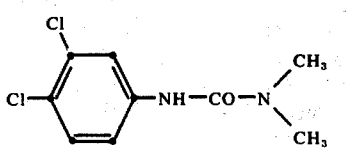

and
 iii. 3-amino-1,2,4-triazole of the formula

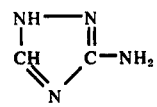

in admixture in a ratio by weight of substantially between 2:1:1 to 1:2:1 to 1:1:2, possess an especially broad and selective herbicidal activity against weeds on uncropped land.

The active compounds of the instant synergistic combinations are precisely defined by formulae (1a), (1b), (2a) and (3a) above, and all three are individually well known.

Surprisingly, the herbicidal effectiveness of the particular new synergistic combinations of active compounds according to the present invention is substantially higher than the sum of the separate effects of the individual active compounds. This is not merely a supplementary or additive effect, but rather a genuine synergistic effect which was not to be foreseen. Significantly, this synergistic effect is particularly great when limited to specific ratios of concentration as noted above.

Advantageously, the synergistic combinations of active compounds according to the present invention are markedly superior to known active compounds conventionally used for weed control in agricultural crops, especially for total herbicidal control of weeds on paths, squares or broad area patches, railway embankments, and waste land. The instant synergistic combinations of active compounds therefore represent a valuable contribution to the art of weed control agents.

The ratio by weight of the active compounds in the instant synergistic combinations may be varied within a certain critical range. In general, the given combination of active compounds is in a ratio by weight of about 1:2 based on two individual components at a time, i.e. in a ratio by weight of substantially between about 2:1:1 through 1:2:1 to 1:1:2 for compounds (1a): (2a): (3a), as aforesaid, as well as for compounds (1b):(2a):(3a). In the case of the synergistic combination on only two of the active compounds in question, i.e. compound (1a) with either compound (2a) or compound (3a) or compound (1b) with either compound (2a) or compound (3a), the ratio by weight is still 1:2, and preferably 1:1, based on the combinations (1a):(2a) and (1a):(3a), as well as (1b):(2a) and (1b):(3a), respectively.

Advantageously, the instant synergistic combinations of active compounds have a very favorable herbicidal activity against weeds on uncropped land.

The term weeds as used herein is to be considered in the widest sense and thus is to be understood to mean all plants which usually occur as contamination of agricultural crops, or as otherwise undesired plants or vegetation for the particular purpose in question.

The synergistic combinations usable according to the present invention evince an extremely strong herbidical power. Such synergistic combinations are therefore particularly suitable for the total destruction of weeds. The effect starts soon after application and is long lasting.

Significantly, it is also possible to destroy weeds growths which contain weeds which are particulary difficult to combat, such as hard grasses, sorrel, crowfoot, mugwort, hawkweed, broadleaf plantain, knapweed, dandelion, and the like.

The instant synergistic combinations show a particularly pronounced effect against herbaceous plants such as St. John's wort, mint and milfoil.

The synergistic combinations according to the present invention can be applied prophylactically to soil on which there is no growth, but are preferably applied onto the existing weed growth.

The particular synergistic combinations of active compounds according to the instant invention can be utilized, if desired, in the form of the usual formulations or compositions with conventional inert (i.e. plant compatible or herbicidally inert) pesticide diluents or extenders, i.e. diluents or extenders of the type usable in conventional pesticide formulations or compositions, e.g. conventional pesticide dispersible carrier vehicles, such as solutions, emulsions, suspensions, emulsifiable concentrates, spray powders, pastes, soluble powders, dusting agents, granules, etc. These are prepared in known manner, for instance by extending the synergistic combination of active compounds with conventional pesticide dispersible liquid diluent carriers and/or dispersible solid carriers optionally with the use of carrier vehicle assistants, e.g. conventional pesticide surfaceactive agents, including emulsifying agents and/or dispersing agents, whereby, for example, in the case where water is used as diluent, organic solvents may be added as auxiliary solvents. The following may be chiefly considered for use as conventional carrier vehicles for this purpose: inert dispersible liquid diluent carriers including inert organic solvents, such as aromatic hydrocarbons (e.g. benzene, toluene, xylene, etc.), halogenated, especially chlorinated, aromatic hydrocarbons (e.g. chlorobenzenes), paraffins (e.g. petroleum fractions), chlorinated aliphatic hydrocarbons (e.g. methylene chloride, etc.), alcohols (e.g. methanol, ethanol, propanol, butanol, etc., ethers, ether-alcohols (e.g. glycol monomethyl ether, etc.), amines (e.g. ethanolamine, etc), amides (e.g. dimethyl formamide, etc.), sulfoxides (e.g. dimethyl sulfoxide, etc.), ketones (e.g. acetone, etc.), and/or water; as well as inert dispersible finely divided solid carriers, such as ground natural minerals (e.g. kaolins, alumina, silica or quartz, chalk, i.e. calcium carbonate, talc, kieselguhr, etc.), and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as nonionic and/or anionic emulsifying agents (e.g. polyethylene oxide esters of fatty acids, polyethylene oxide ethers of fatty alcohols, alkyl sulfonates, aryl sulfonates, etc., and especially alkyl aryl-polyglycol ethers, magnesium stearate, sodium oleate, etc.); and/or dispersing agents, such as lignin, sulfite waste liquors, methyl cellulose, etc.

As will be appreciated by the artisan, the synergistic combination of active compounds according to the instant invention may be employed alone or in the form of carrier composition extended mixtures with such solid and/or liquid dispersible carrier vehicles and/or with other known compatible active agents, such as other herbicides, fungicides, bactericides, etc., if desired, or in the form of particular dosage preparations for specific application made therefrom, such as solutions, emulsions, suspensions, powders, pastes, and granules which are thus ready for use.

As concerns commercially marketed preparations, these generelly contemplate carrier composition overall mixtures in which the synergistic combination of active compounds is present in a total amount substantially between about 0.1-95%, and preferably 0.5-90%, by weight of the overall carrier composition extended mixture, whereas overall carrier composition mixtures suitable for direct application or field application generally contemplate those in which the synergistic combination of active compounds is present, e.g. in the form of a dosage unit preparation containing substantially between about 5-50, and preferably 10-20, kilograms of the synergistic combination per hectare of soil being treated, i.e. irrespective of the presence or absence of the carrier vehicle. Thus, the present invention contemplates selective herbicidal compositions which comprise overall carrier composition extended mixtures of a conventional dispersible carrier vehicle such as (1) a dispersible carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the synergistic combination of active compounds, e.g. in a ratio of 2:1:1 through 1:2:1 to 1:1:2 therebetween for the compounds (1a):(2a):(3a), or in a ratio of 1:2, and preferably 1:1, therebetween for the two compounds (1a):(2a) or (1a):(3a), as aforesaid, which is effective for the purpose in question and which is generally between about 0.1-95% by weight of the overall carrier composition extended mixture. Specifically, the synergistic combination of the active compounds may be applied in the form of a herbicidal composition to a surface area, for example, railway tracks, fence lines, pathes or other places where weeds cause damage, impede drainage or lead to increased fire or corrosion risks, in concentrations such that said synergistic combination is distributed in a dosage of substantially between about 5-50 kg per hectare of soil being treated, preferably 10-20 kg per hectare, although it will be appreciated that in connection with the post-emergence use of the instant synergistic combinations, as well as the pre-emergence use thereof, the concentration may be varied within a fairly wide range, depending on various factors such as the composition of the synergistic combination, the conditions of cultivation, soil, weeds, e.g. weeds particularly difficult to combat in crop cultivation, weather, and the like. However, generally the pre-emergence range of concentration of the synergistic combination will be 0.1 to 95% by weight of the overall mixture as aforesaid, while the post-emergence range of such synergistic combination will be between about 5-50 kg per hectare, as aforesaid, i.e. irrespective of the presence or absence of the carrier vehicle.

Furthermore, the present invention contemplates methods of selectively killing, combating or controlling undesired plants, e.g. weeds and the like, especially weeds particularly difficult to combat on uncropped land, which comprise applying to at least one of (a) such weeds and (b) their habitat, i.e. the locus to be protected, a herbicidally effective or toxic amount of a herbicidal composition containing the particular synergistic combination of active compounds of the invention alone or together in an overall mixture with a carrier vehicle as noted above. The instant formulations or compositions are applied in the usual manner, for example, by spraying, atomixing, scattering, dusting, watering, sprinkling, pouring, vaporising, and the like, whether for post-emergence application to the weeds, which is the preferred procedure, or pre-emergence application to the soil, and generally in amounts such that, regardless of the presence of absence of the carrier vehicle and/or other compatible active agents, substantially between about 5–50 kg. of the synergistic combination are distributed per hectare of soil being treated.

The favorable herbicidal effect of the instant combinations of active compounds can be seen from the following Example. Whereas the individual active compounds exhibit deficiencies with regard to their herbicidal effect, the instand synergistic combinations have a very broad and long lasting activity against weeds, which exceeds the simple sum of the individual effects.

In the case of selective herbicides, especially those selective for weeds as opposed to valuable agricultural crops, a synergistic effect is always considered to be present when, with the same amounts applied, the herbicidal effect of the given combination of active compounds on the weeds is equal to or greater than the herbicidal effect of the more effective individual active compound alone, while at the same time the herbicidal effectiveness of the combination of active compounds on the cultivated plant itself is less than the herbicidal effectiveness on such cultivated plant of that individual active compound which is most compatible with the cultivated plant. In these cases, therefore, the selectivity, and thus the herbicidal index, is clearly increased. In the case of combinations of active compounds without synergistic effect, a mere broadening of the spectrum of activity is expected, but not an increase of the selectivity. Generally, without synergism, the sum of the effects to be expected from a given combination of active compounds understandably depends on the mixing ratio and lies between the individual effect of the less effective and that of the more effective individual active compound.

From the Tables of the Example it can clearly be seen that the combinations of active compounds according to the invention show a genuine synergistic effect. The herbicidal effect of the combination of active compounds is always at least as high as the herbicidal effect of the more effective individual active compound.

EXAMPLE 1

Spraying test on existing weeds

Active compound preparations:

i. containing 70% by weight of either 3-methylmercapto4-amino-6-isopropyl-1,2,4-triazin-5-one, or 3-methylmercapto4-amino-6-tert.-butyl-1,2,4-triazin-5-one, respectively, 5% by weight of a mixture of an arylsulfonic acid-formaldehyde condensate + ethylpolyglycol-ether, 2% by weight of lignin sulfonate and 23% by weight of quartz powder.

ii. containing 80% by weight of N'-(3,4-dichlorophenyl)-N,N-dimethyl-urea, 5% by weight of lignin-sulfonate, 3.5% by weight of highly disperse silica, 1.5% by weight of naphthalene sulfonate and 10% by weight of colloidal kaolin.

iii. containing 100% by weight of 3-amino-1,2,4triazole.

The preparations are brought to the requisite concentration by dilution with water. Such diluted preparations are then applied to plots showing similar weed growth, using a conventional spraying apparatus and an amount of liquor of 750 litres per hectare. It will be realized that the particular active compound concentration in the preparation is of no importance; only the amount of active compound or synergistic combination applied per unit area is decisive.

After 2 months and after 6 months the plant growth, which initially showed a degree of area coverage of 100%, is examined and the remaining growth is assessed as a precentage degree of cover of the vegetation. A degree of cover of 100% denotes that the cover at the time of the assessment is as great as the cover at the start. 0% denotes that all weeds have been destroyed. Furthermore the surviving varieties of plants are recorded.

The particular active compounds or combinations of active compounds tested, the amounts used per unit area and the results obtained will be seen from the following Table 1.

Table 2 below, in similar manner, gives the impairment of the individual varieties of plants by the particular active compounds or combinations of active compounds tested.

It will be realized that the amounts used per unit area noted below are of the active compounds themselves or of the combinations of active compounds, irrespective of whether carrier vehicles and/or surface-active agents are present in the corresponding formulations.

Table 1

| Active Compound or Combination of Compounds | Amount of Active Compound or Combination of Active Compounds Applied in kg/ha | Mixing ratio of the active compounds | Degree of Cover in % | | | |
|---|---|---|---|---|---|---|
| | | | after 2 months | | after 6 months | |
| | | | +) grasses | broad-leaved weeds ++) | +) grasses | broad-leaved weeds |
| (1a) 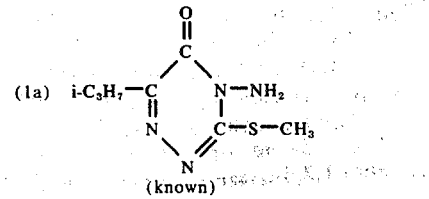 (known) | 3 | | 30 | 60 | 35 | 65 |
| | 4 | | 25 | 50 | 30 | 60 |
| | 6 | | 10 | 40 | 15 | 55 |
| | 12 | | 2.5 | 30 | 5 | 50 |

Table 1-continued

| Active Compound or Combination of Compounds | Amount of Active Compound or Combination of Active Compounds Applied in kg/ha | Mixing ratio of the active compounds | Degree of Cover in % | | | |
|---|---|---|---|---|---|---|
| | | | after 2 months | | after 6 months | |
| | | | +) grasses | broad-leaved weeds ++) | +) grasses | broad-leaved weeds |
| (2a) Cl—⌬—NH—CO—N(CH₃)₂ (with Cl) (known) | 3<br>4<br>6<br>12 | | 25<br>20<br>10<br>5 | 75<br>75<br>65<br>50 | 25<br>20<br>20<br>15 | 75<br>80<br>75<br>70 |
| (3a) (triazine structure) (known) | 3<br>4<br>6<br>12 | | 25<br>25<br>20<br>10 | 70<br>65<br>60<br>40 | 25<br>25<br>25<br>30 | 75<br>75<br>75<br>70 |
| (1b) t-C₄H₉— (triazinone with S-CH₃, N-NH₂) (known) | 3<br>4<br>6<br>12 | | 30<br>25<br>10<br>2.5 | 60<br>50<br>40<br>30 | 35<br>30<br>15<br>5 | 65<br>60<br>55<br>50 |
| (2a) + (3a) (known) | 3<br>4<br>12 | 1 : 1<br>1 : 1<br>1 : 1 | 30<br>20<br>5 | 60<br>50<br>30 | 35<br>25<br>10 | 65<br>60<br>50 |
| (1a) + (3a) | 12 | 1 : 1 | 2.5 | 25 | 10 | 30 |
| (1a) + (2a) | 12 | 1 : 1 | 2.5 | 25 | 5 | 40 |
| (1a) + (2a) + (3a) | 12 | 2 : 1 : 1 | 0 | 20 | 2.5 | 25 |
| (1a) + (2a) + (3a) | 12 | 1 : 2 : 1 | 0 | 25 | 5 | 25 |
| (1a) + (2a) + (3a) | 12 | 1 : 1 : 2 | 2.5 | 20 | 5 | 30 |
| (1a) + (2a) + (3a) | 12 | 1 : 1 : 1 | 0 | 5 | 2.5 | 10 |

+) "grasses" means: *Agropyron repens, Dactylis glomerata, Bromus erectus, Calamagrostis epigeios, Echinochloa crus-galli.*
++) "broad-leaved weeds" mean those which occur on roads or industrial areas.

Table 2

| Active Compound or Combination of Active Compounds (as in Table 1) | Amount of Active Compound or Combination of Active Compound Applied in kg/ha | Mixing ratio of the active compounds | *Plantago* (broad-leaved plantain) | *Achillea* (milfoil) | *Rumex* (sorrel) | *Hypericum* (St. John's wort) | *Mentha* (mint) | *Taraxacum* (dandelion) |
|---|---|---|---|---|---|---|---|---|
| (1a) (known) | 12 | | MR | MR | MS | S | MR | MS |
| (1b) (known) | 12 | | MR | MR | MS | S | MR | MS |
| (2a) (known) | 12 | | R | MR | R | R | MR | MR |
| (3a) (known) | 12 | | MR | MS | MR | MR | MS | MS |
| (2a) + (3a) (known) | 12 | 1 : 1 | MR | MS | MS | MR | MS | MS |
| (1a) + (3a) | 12 | 1 : 1 | MS | MS | MS | S | MS | MS |
| (1a) + (2a) | 12 | 1 : 1 | MS | MS | MS | S | MS | MS |
| (1a) + (2a) + (3a) | 12 | 1 : 1 : 1 | S | S | S | S | S | S |

R = resistant: no impairment of plant growth by the active compound or combination.
MR = moderately resistant: slight impairment of the plant growth by the active compound or combination, rapid fresh growth.
MS = moderately sensitive: strong impairment of the plant growth by the active compound or combination, delayed fresh growth.
S = sensitive: plant destroyed by active compound or combination; no fresh growth.

It will be realized by the artisan that all of the foregoing synergistic compositions of active compound combinations contemplated by the present invention possess the desired selective herbicidal properties, as well as a comparatively low toxicity toward warm-blooded creatures, enabling such synergistic combinations of active compounds to be used with correspondingly favorable compatibility with respect to warm-blooded creatures for more effective control and/or elimination of weeds, by application of such synergistic combination of active compounds to such weeds and/or their habitat. Nevertheless, the instant synergistic combinations possess total herbicidal action when used in large quantities, although selective herbicidal action is obtained when used in smaller quantities. As contemplated herein, the term "weeds" is meant to include not only weeds in the narrow sense, but also in the broad sense, whereby to cover all plants and vegetation considered undesirable for the particular purposes in question.

It will be appreciated that the instant specification and examples are set forth by way of illustration and not limitation, and that various modifications and changes may be made without departing from the spirit and scope of the present invention.

1. A herbicidal composition which consists essentially of a herbicidally effective amount of a combination of either 3-methylmercapto-4-amino-6-isopropyl-1,2,4-triazin-5-one or 3-methylmercapto-4-amino-6-tert.-butyl-1,2,4-triazin-5-one of the formula

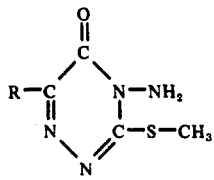

wherein

R represents i-$C_3H_7$ or t-$C_4H_9$, with N'-(3,4-dichlorophenyl)-N,N-dimethyl-urea of the formula

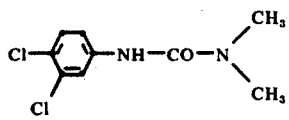

in admixture in a ratio by weight of substantially 1:1, and an inert carrier.

2. Composition according to claim 1 wherein said combination is in the form of a carrier composition mixture with a dispersible carrier vehicle, in which said combination is present in a herbicidally effective amount and constitutes substantially between about 0.1–95% by weight of the carrier composition mixture.

3. Composition according to claim 1 wherein said combination is in the form of a carrier composition mixture with a dispersible carrier vehicle selected from the group consisting of (1) a dispersible finely divided carrier solid and (2) a dispersible carrier liquid selected from the group consisting of an organic solvent, water and mixtures thereof containing a surface-active agent selected from the group consisting of anionic emulsifying agents, non-ionic emulsifying agents, dispersing agents, and mixtures of such agents, in which said combination is present in a herbicidally effective amount and constitutes substantially between about 0.1–95% by weight of the carrier composition mixture.

4. Method of using a composition according to claim 1 for combating weeds which comprises applying to the locus thereof a herbicidally effective amount of such herbicidal composition containing a combination according to claim 1.

5. Method according to claim 4 wherein said combination is used in the form of a carrier composition mixture with a dispersible carrier vehicle, in which said combination is present in a herbicidally effective amount and constitutes substantially between about 0.1–95% by weiight of the carrier composition mixture.

6. Method according to claim 4 wherein said combination is used in the form of a carrier composition mixture with a dispersible carrier vehicle selected from the group consisting of (1) a dispersible finely divided carrier solid and (2) a dispersible carrier liquid selected from the group consisting of an organic solvent, water and mixtures thereof containing a surface-active agent selected from the group consiting of anionic emulsifying agents, non-ionic emulsifying agents, dispersing agents, and mixtures of such agents, in which said combination is present in a herbicidally effective amount and constitutes substantially between about 0.1–95% by weight of the carrier composition mixture.

7. Method according to claim 4 wherein said herbicidal composition is applied to land not used for crops, in an amount such that said combination is distributed in a dosage of substantially between about 5–50 kg/hectare of soil being treated.

* * * * *